United States Patent [19]
Freeman et al.

[11] Patent Number: 5,624,437
[45] Date of Patent: Apr. 29, 1997

[54] HIGH RESOLUTION, HIGH SPEED, PROGRAMMABLE LASER BEAM MODULATING APPARATUS FOR MICROSURGERY

[76] Inventors: Jerre M. Freeman, 6485 Poplar Ave., Memphis, Tenn. 38119; Ronald G. Driggers, 1121 Natchez Point #95, Memphis, Tenn. 38104; Roy E. Williams, 3982 Mary Lee Dr., Memphis, Tenn. 38116; Carl E. Halford, 1538 Cordova Mills Cove, Cordova, Tenn. 38018; William R. Clayton, 3573 Philwood Ave., Memphis, Tenn. 38122

[21] Appl. No.: 411,944

[22] Filed: Mar. 28, 1995

[51] Int. Cl.$^6$ .................................................. A61D 5/02
[52] U.S. Cl. ................................ 606/12; 606/5; 606/10; 606/13
[58] Field of Search ........................................ 606/2–19

[56] References Cited

U.S. PATENT DOCUMENTS

| | | | |
|---|---|---|---|
| 4,579,430 | 4/1986 | Bell | 606/10 |
| 4,732,148 | 3/1988 | L'Esperance, Jr. | 606/5 |
| 4,911,711 | 3/1990 | Telfair et al. | 606/5 |
| 5,219,344 | 6/1993 | Yoder, Jr. | 606/5 |
| 5,281,211 | 1/1994 | Parel et al. | 606/5 |
| 5,312,320 | 5/1994 | L'Esperance, Jr. | 606/5 |
| 5,350,374 | 9/1994 | Smith | 606/5 |

OTHER PUBLICATIONS

Texas Instruments brochure titled "DMD Projecting a Brighter Future." Oct. 1994. (2 pages).
Texas Instruments publication titled "DMD Display 1994." pp. 1–6.
Texas Instruments publication titled "Deformable–Mirror Spatial Light Modulators." Aug. 1989. pp. 1–17.
Texas Instruments reprint of article titled "Digital micromirror array for projection TV" from the Jul. 1994 edition of Solid State Technology magazine.
Aura Systems, Inc. brochure for AuraScope Projection System.

*Primary Examiner*—David M. Shay
*Attorney, Agent, or Firm*—Jack Lo

[57] ABSTRACT

A high speed, high resolution, programmable laser beam modulating apparatus includes a computer connected to a high resolution micromirror array having individually addressable and movable mirrors. The computer is also connected to a pulsed laser for controlling the emission thereof. A beam homogenizing optic changes an ablating input beam from the laser into a homogeneous beam having a uniform cross-sectional energy density. The mirrors are movable between an "on" position for reflecting a portion of the homogeneous beam onto a cornea, and an "off" position for reflecting the beam away from the cornea. The computer is programmed to move the mirrors to the "on" position in a series of predetermined patterns, and the remaining mirrors to the "off" position, and to fire the laser during the presence of each pattern, so that corresponding patterns of tissue on the cornea are successively ablated therefrom. The ablated patterns are overlaid on each other, so that they combine to produce a contour change in the cornea and correct a refractive error thereof.

13 Claims, 2 Drawing Sheets

HIGH RESOLUTION, HIGH SPEED, PROGRAMMABLE LASER BEAM MODULATING APPARATUS FOR MICROSURGERY

BACKGROUND OF THE INVENTION

1. Field of the Invention

This invention relates generally to ophthalmological surgery, specifically to a programmable apparatus for modulating a laser beam at high speed for ablating a high resolution corrective profile on a cornea.

2. Prior Art

Myopia (nearsightedness), hyperopia (farsightedness), and astigmatism are refractive errors of the eye that are correctable by reshaping the surface contour of the cornea. A typical procedure involves measuring the shape of a patient's cornea, determining a suitable corrective profile, and reshaping the cornea to match the corrective profile by ablating away a suitably shaped volume of tissue with a spatially manipulated beam from a pulsed laser.

U.S. Pat. No. 4,911,711 to Telfair et al. (1990) and U.S. Pat. No. 5,219,344 to Yoder, Jr. (1993) show laser surgical devices with indexable discs or masks for modulating the cross-sectional shape of an ablating beam. Each mask includes a series of graduated apertures, which are sequentially indexed into alignment with the beam for changing the shape of the ablated area on a cornea. More than one laser pulse may be directed at the cornea through each aperture; the number of pulses fired through each aperture depends on the ablation depth required. Therefore, a desired corrective contour on the cornea is produced by exposing different areas thereon to the beam. However, a large number of different masks must be provided for the large number of possible corrections. Furthermore, the resultant surface contour has a stairstep or terrace shape, wherein the size of the steps are determined by the size difference between adjacent apertures. Because the number of apertures on each mask is physically limited by the diameter thereof, the contours producible are very limited in lateral resolution, i.e., they are rough.

U.S. Pat. No. 5,312,320 to L'Esperance, Jr. (1994) shows a surgical laser device with a partially reflective mirror having varying reflectance along the radius thereof. An input beam having uniform intensity across its diameter is passed through the mirror, which produces an output beam with a precise intensity profile in both the reflected and transmitted components, either of which is usable for ablating the entire surgical zone of a cornea simultaneously. The amount of tissue ablated at any given point is proportional to the laser energy impinging thereon, so that a desired corrective profile can be obtained by using a mirror having a suitable reflectance profile. However, a great number of mirrors having different reflectance profiles are needed for the great number of possible corrections. Furthermore, if a patient requires a correction which does not have a matching mirror, then the closest mirror must be used to produce a less-than-optimal correction.

U.S. Pat. No. 5,281,211 to Parel et al. (1994) shows a surgical laser device with an axicon lens for marking circumferentially arranged spots on a cornea. In another embodiment, masks are used for selectively blocking portions of the beam. This device has the same disadvantages associated with other mask devices.

A further disadvantage of all prior art laser surgical devices with indexable masks is that changing apertures is a slow process, so that a typical operation can take several minutes or more. Such a long surgical procedure is prone to errors, because the eye may shift during the operation.

OBJECTS OF THE INVENTION

Accordingly, an object of the present invention is to provide a laser beam modulating apparatus for modulating each of a series of pulsed laser beams for ablating a series of predetermined patterns in successive layers on a cornea, so as to subtract a total volume of tissue having a predetermined shape for effecting a desired refractive correction.

Another object of the present invention is to provide a laser beam modulating apparatus that is adjustable between rapid beam pulses for changing the ablating pattern of each pulse, so that a typical operation will last just seconds.

Still another object of the present invention is to provide a laser beam modulating apparatus that can modulate a beam at a high resolution for producing a substantially smooth contour on a cornea.

Other objects of the present invention will become apparent from a study of the drawing figures and the following description.

SUMMARY OF THE INVENTION

A laser beam modulating apparatus achieves the aforementioned objects with a micromirror array positioned in the beam path of a pulsed laser. A beam homogenizing optic is positioned between the laser and the micromirror array for providing the array with a beam having a uniform cross-sectional energy distribution. The micromirror array includes more than a million tiny mirrors that are each independently addressable and tiltable about its own pivot. A computer connected to the array is programmed for configuring the mirrors to reflect a predetermined light pattern onto a cornea during each firing of the pulsed laser. The configuration of the mirrors is changed between each pulse, so that a series of different but overlapping patterns are ablated from the cornea. After the last pulse, a total volume of tissue having a predetermined shape is thus removed, so that the remaining corneal tissue is given a predetermined profile or surface contour for effecting a refractive change.

DRAWING REFERENCE NUMERALS

| | |
|---|---|
| 10. Micromirror Array | 11. Interface Board |
| 12. Computer | 13. Beam Homogenizing And Collimating Optic |
| 14. Beam Reimaging Optic | 15. Mirrors |
| 16. Pivot | 17. Substrate |
| 18. Pulsed Laser | 19. Cornea |
| 20–26. Logic Blocks | L1–L3. Ablated Layers |
| B1–B4. Laser Beams | |

DESCRIPTION—FIG. 1

Figure 1:
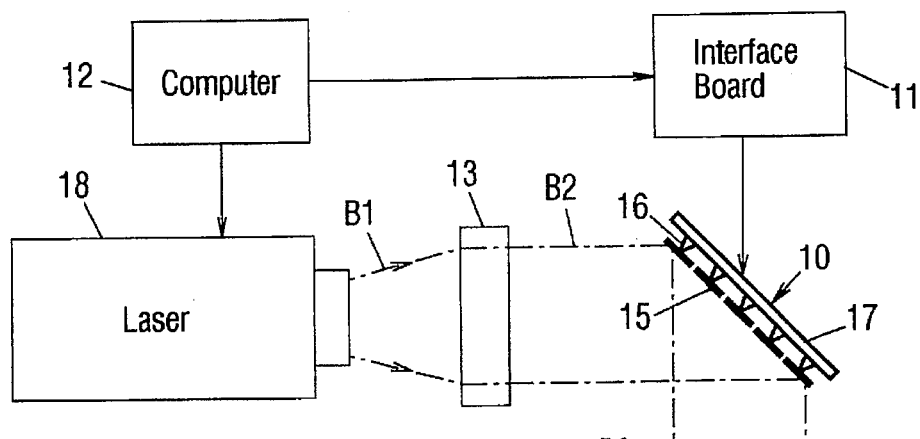
FIG. 1 is a schematic diagram of a laser beam modulating apparatus in accordance with a preferred embodiment of the invention.

In accordance with a preferred embodiment of the invention shown in the schematic diagram of FIG. 1, a laser beam modulating apparatus includes a micromirror array 10, an interface board 11, a computer 12, a conventional beam homogenizing and collimating optic 13, and a conventional reimaging optic 14. Micromirror array 10 will be available from Texas Instruments, Dallas, Texas, under the trademark "Digital Micromirror Device."

Micromirror array 10 is a 2,048×1,152 x-y array of 16 μm aluminum mirrors, although only five individual mirrors 15 are shown, edge-on, in this example for simplicity. In one embodiment, each mirror 15 is supported on a pivot 16 that is attached to a substrate 17. Micromirror array 10 contains its own addressing circuitry (not shown) for each mirror 15. Interface board 11 converts the signals from computer 12, which may be any suitable type of computer, to the waveforms required by the addressing circuitry of micromirror array 10. e.g., if computer 12 is an IBM-compatible personal computer (not shown), then interface board 11 would plug into an expansion slot therein. Addressing schemes and hardware support data for micromirror array 10 are well disclosed in literature available from Texas Instruments.

Each mirror 15 is individually addressable by computer 12 through interface board 11, and is tiltable about its own pivot 16 for reflecting light from a pulsed ultraviolet laser 18 to or away from a target or cornea 19. Mirrors 15 have a response time of about 10 μs, and are capable of tilting at a repetition rate of 5 kHz or higher. For operation with ultraviolet laser 18, mirrors 15 may be coated with additional or different reflective materials, which are well known in the art, that are optimized for reflecting ultraviolet light. In this example, mirrors 15 are all configured in the "on" position to reflect laser light onto cornea 19. Mirrors 15 are also configurable or tiltable to the "off" position (not shown), to be explained further infra, to reflect laser light away from cornea 19. The spaces between individual mirrors 15 are exaggerated in the figures for clarity, but an actual array would have much smaller gaps. The firing of pulsed laser 18 is also controlled by computer 12. For ophthalmological surgery, laser 18 would typically be an Argon Fluoride laser, although any other suitable type of laser can be used.

Beam homogenizing and collimating optic 13 changes a raw input beam B1 from an initial Gaussian distribution, i.e., one having an energy cross section in the shape of a bell curve, to a homogenous and collimated beam B2 with a uniform cross-sectional energy density. Optic 13 also reduces the divergence of beam B2, and increases the width thereof to illuminate a maximum circular area on micromirror array 10, which in this example is at least about 20 mm wide. Beam reimaging optic 14 resizes the reflected beam B3 into an output beam B4 of a suitable size for ablating a desired zone on cornea 16, which would typically be about 7 mm across. Beam homogenizing and collimating optic 13 and reimaging optic 14 are both conventional components that are well known in the art.

The ablation depth on cornea 19 achieved by each pulse of output beam B4 depends on its fluence, or energy density, at the point of impingement. The relationship between fluence and ablation depth on corneas is well known in the art, and substantially follows the formula a=0.002198F−0.1232, where "a" is the ablation depth in micrometer, and "F" is the fluence in millijoules per square centimeter. A typical level of fluence used in ophthalmological surgery is 200 mJ/cm$^2$ for a per pulse ablation depth of about 0.3164 μm. Because beam B4 has a uniform energy distribution, it will achieve the same ablation depth at all points therein.

By configuring a predetermined pattern (not shown) of mirrors 15 to the "on" position and the remaining ones to the "off" position, then firing laser 18, a corresponding pattern of tissue will be ablated from cornea 19. By reconfiguring the "on/off" pattern of mirrors between laser pulses, a series of different, overlaying patterns of tissue can be ablated from cornea 19. The ablation patterns subtract a predetermined volume of tissue from cornea 19, so that the remaining surface thereon is given the corrective profile. The desired corrective profile for any particular eye depends on its type of error: an eye with myopia would have more volume at the center of the cornea removed than at the periphery, whereas an eye with hyperopia would have less volume at the center of the cornea removed than at the periphery. Such corrective profiles are well known in the art.

The total number of pulses required for each surgical operation depends on the maximum ablation depth required. e.g., a particular mirror 15 corresponding to a position on cornea 19 that requires the deepest ablation would be configured in the "on" position for reflecting all the pulses, whereas another mirror 15 corresponding to a position on cornea 19 that requires less ablation would be configured in the "on" position for reflecting a suitable number of initial pulses, then configured in the "off" position to reflect the remainder of the pulses away from cornea 19.

DESCRIPTION—FIG. 2

Figure 2:
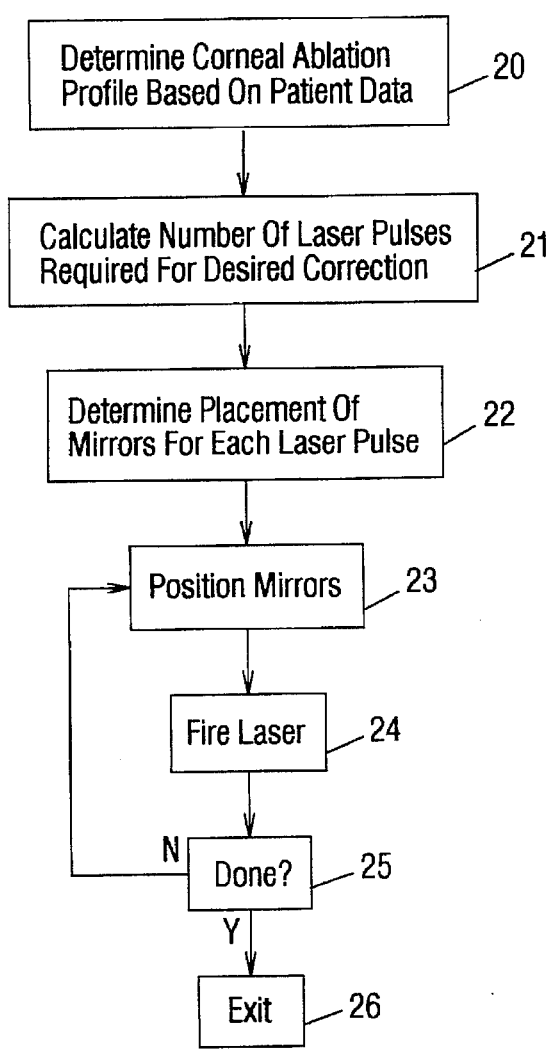
FIG. 2 is a flow diagram of the logical sequence of operations of the laser beam modulating apparatus.
Figure 3:
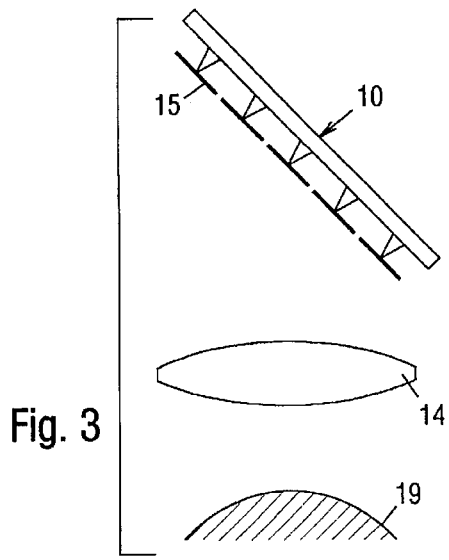
FIGS. 3–6 illustrate an exemplar procedure for correcting a refractive error of the eye using the laser beam modulating apparatus.

Computer 12 (FIG. 1) is programmed for performing the sequence of operations shown in the flow diagram of FIG. 2. At block 20, the corrective profile is determined by using patient data and methods well known in the art. The difference between the original profile and the corrective profile is the total volume to be removed. The total number of pulses required for the deepest part of the correction is calculated at block 21. e.g., if a beam with a fluence of 200 mJ/cm$^2$ is used, then according to the equation described above, 111 pulses will be required for ablating a correction profile having a maximum depth of about 35 μm.

The position of each mirror 15 for each laser pulse is determined at block 22, i.e., a series of mirror "on/off" patterns are determined. Each pattern would correspond to a "slice" of the volume to be removed. Mirrors 15 are positioned for the first pattern at block 23. Laser 18 (FIG. 1) is triggered at block 24 to fire a single pulse for ablating the previously set pattern. If all the patterns are not completed at block 25, the operation returns to block 23, so that the next pattern is configured for the next laser pulse. When all the patterns are completed, the routine exits at block 26.

DESCRIPTION—FIG. 3–6

A simplified myopic correction procedure is shown in FIGS. 3–6 as a typical use of the laser beam modulating apparatus. Micromirror array 10 and cornea 19 are shown in their initial conditions before the first pulse in FIG. 3.

Figure 4:
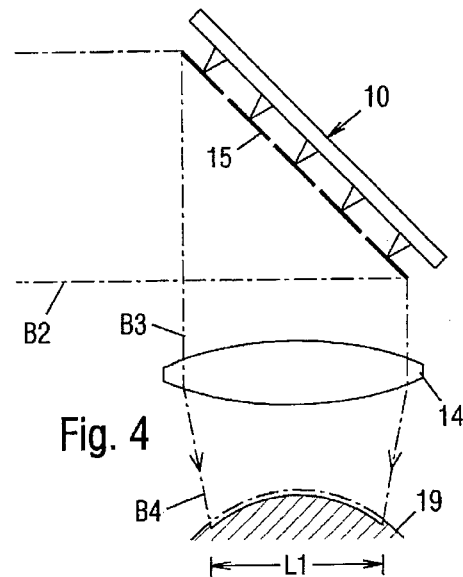

In this example, all mirrors 15 are configured in the "on" position for an initial pattern that ablates the maximum surgical zone on cornea 19. As shown in FIG. 4, the full width of pulsed beam B2 is reflected by mirrors 15 through reimaging optic 14 as output beam B4, so that a first layer L1 is ablated from cornea 19. The original surface of cornea 19 is shown as a hidden line for reference.

Figure 5:
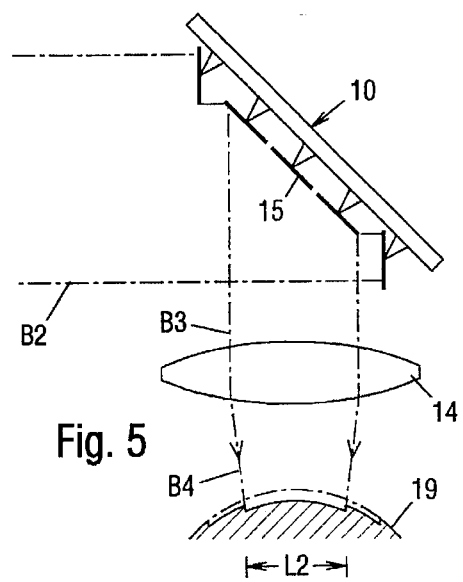

As shown in FIG. 5, mirrors 15 are reconfigured in another pattern for the second laser pulse. The outer mirrors 15 are tilted to the "off" position to reflect the outer portions of beam B2 away from cornea 19. The degree of tilt is shown exaggerated for clarity. The middle three mirrors 15 remain in the "on" position to reflect a narrower output beam B4 onto cornea 19, so that a narrower second layer L2 is ablated therefrom.

Figure 6:
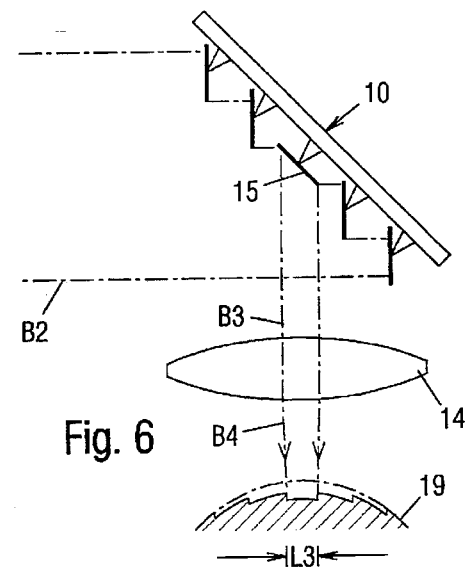

As shown in FIG. 6, mirrors 15 are reconfigured in yet another pattern for the third laser pulse. All mirrors 15, except the one in the center, are tilted to the "off" position to reflect most of beam B2 away from cornea 19. A very narrow output beam B4 is reflected by the only "on" mirror 15 at cornea 19, so that a very narrow third layer L3 is ablated therefrom. Accordingly, the curvature of cornea 19 is reduced for effecting a myopic correction.

In this example, the small number of mirrors 15 produce a rough stairstep surface on cornea 19, but in actual use, the 2,048×1,152 array of mirrors 15 will produce a substantially smooth or high resolution curve. Also in actual use, the number of laser pulses required would likely be greater, but most corrections would require no more than a few hundred pulses. For ophthalmological surgery, the generally accepted maximum repetition rate for pulsed laser ablation is 50 Hz. Accordingly, micromirror array 10 can be reconfigured at 50 Hz, and laser 18 (FIG. 1) can be fired at 50 Hz. Therefore, most procedures will take just a few seconds.

The laser beam modulating apparatus can be easily programmed for sculpting a cornea into any shape necessary to correct any refractive error, including myopic, hyperopic, and astigmatic conditions.

CONCLUSIONS, RAMIFICATIONS, AND SCOPE

Accordingly the reader will see that we have provided a laser beam modulating apparatus that can be programmed to modulate an ablating laser beam to sculpt a suitable corrective profile on a cornea for correcting any refractive error. It can reshape each laser pulse, and it can be reconfigured at a high rate, so that most operations will take just a few seconds. It can also sculpt a substantially smooth corrective profile on a cornea.

Although the above descriptions are specific, they should not be considered as limitations on the scope of the invention, but only as examples of the preferred embodiment. Many other ramifications and variations are possible within the teachings of the invention. For example, other micromirror arrays can be used, such as the one that will be sold under the trademark "Aurascope Actuated Mirror Array" by Aura Systems, Inc., El Segundo, Calif. Micromirror arrays of other sizes and resolutions can be used, although higher resolutions are naturally preferable for producing smoother corrective profiles. The reimaging optic can be adapted for collimating the output beam. Other suitable types of computers can be used for driving the micromirror array, including an embedded microcontroller or microprocessor. Other types of lasers can be used. The computer can be programmed for controlling the micromirror array and the laser in a different sequence of operations. Additional optics can be used for slightly unfocusing the laser image impinging upon the cornea to reduce the stairstep effect, so as to produce an even smoother corrective profile. Each "on" mirror pattern may direct more than one laser pulse onto the cornea. Whether a tilted mirror is called "off" or "on" depends on how the micromirror array is positioned, e.g., the array can be positioned so that a tilted mirror reflects laser light onto the cornea, in which case the tilted position will be the "on" position.

In addition to the application described, the laser beam modulating apparatus can be used to deliver excimer laser energy to other areas of the eye and other tissues for treatment. With proper adaptation of the mirrors and optics, the laser beam modulating apparatus can also be used to deliver other forms of laser and light energy for other medical uses. e.g., it can be used with a $CO_2$, Holmium, Erbium, or Yttrium-Aluminum-Garnet laser for cutting, ablating, and altering various tissues; it can be used with a diode laser for the photocoagulation of tissue, such as the retina; it can be used with an Argon, Krypton, or a tunable dye laser for the delivery of green, yellow, and red wavelengths, mainly to the retina; it can also be used for precisely and controllably delivering X-rays or radiation of other wavelengths to structures, tumors, or other areas to be treated. Therefore, the scope of the invention should not be determined by the examples given, but by the appended claims and their legal equivalents.

We claim:

1. A surgical apparatus for receiving, modulating, and redirecting an ablating laser beam onto a target for ablating a surface thereof, comprising:

a micromirror array positioned in said ablating laser beam for reflecting selected portions thereof onto said target, said micromirror array comprising a plurality of independently addressable and movable mirrors, each of said mirrors being movable between an ON position for reflecting an incident portion of said ablating laser beam onto said target, and an OFF position for reflecting said incident portion of said ablating laser beam away from said target; and means for moving a predetermined pattern of said mirrors to said ON position and the remaining mirrors to said OFF position, so as to partly reflect said ablating laser beam onto said target and ablate a corresponding pattern of material from said surface thereof.

2. The surgical apparatus of claim 1, further including a reimaging optic positioned relative to said micromirror array and in said ablating laser beam for resizing said ablating laser beam, so as to ablate a zone of a predetermined size on said target.

3. A surgical apparatus for receiving, modulating, and redirecting an ablating laser beam onto a target for ablating a surface thereof, comprising:

a beam homogenizing optic positioned in said ablating laser beam for modulating said ablating laser beam into a homogeneous beam having a uniform cross-sectional energy distribution;

a micromirror array positioned relative to said beam homogenizing optic and in said homogeneous beam for reflecting selected portions thereof onto said target, said micromirror array comprising a plurality of independently addressable and movable mirrors, each of said mirrors being movable between an ON position for reflecting an incident portion of said homogeneous beam onto said target, and an OFF position for reflecting said incident portion of said homogeneous beam away from said target; and a computer connected to said micromirror array for individually addressing and moving each of said mirrors, said computer being programmable for moving a predetermined pattern of said mirrors to said ON position and the remaining mirrors to said OFF position, so as to partly reflect said homogeneous beam onto said target and ablate a corresponding pattern of material from said surface thereof.

4. The surgical apparatus of claim 3, further including collimating means for collimating said ablating laser beam.

5. The surgical apparatus of claim 3, further including an interface board connected between said computer and said micromirror array.

6. The surgical apparatus of claim 3, further including a reimaging optic positioned relative to said beam homogenizing optic and in said homogeneous beam for resizing said homogeneous beam, so as to ablate a zone of a predetermined size on said target.

7. A surgical laser apparatus for sculpting a surface of a target, comprising:

a laser for emitting an ablating laser beam;

a beam homogenizing optic positioned relative to said laser and in said ablating laser beam for modulating said ablating laser beam into a homogeneous beam having a uniform cross-sectional energy distribution;

a micromirror array positioned relative to said beam homogenizing optic and in said homogeneous beam for reflecting selected portions thereof onto said target, said micromirror array comprising a plurality of independently addressable and movable mirrors, each of said mirrors being movable between an ON position for reflecting an incident portion of said homogeneous beam onto said target, and an OFF position for reflecting said incident portion of said homogeneous beam away from said target; and a computer connected to said micromirror array for individually addressing and moving each of said mirrors, said computer being connected to said laser for triggering the emission thereof, said computer being programmable for moving a predetermined pattern of said mirrors to said ON position and the remaining mirrors to said OFF position, and changing said pattern a plurality of times so as to form a plurality of different patterns, said computer triggering said laser during the presence of each of said different patterns for ablating corresponding patterns of material from said surface of said target to effect a contour change thereon.

8. The surgical laser apparatus of claim 7 wherein said pulsed laser comprises an ultraviolet laser.

9. The surgical laser apparatus of claim 7 wherein said homogeneous beam has a fluence of about 200 mJ/cm$^2$.

10. The surgical laser apparatus of claim 7, further including collimating means for collimating said ablating laser beam.

11. The surgical laser apparatus of claim 7 wherein said mirrors and said laser are moved and triggered, respectively, at about 50 Hz.

12. The surgical laser apparatus of claim 7, further including an interface board connected between said computer and said micromirror array.

13. The surgical laser apparatus of claim 7, further including a reimaging optic positioned relative to said beam homogenizing optic and in said homogeneous beam for resizing said homogeneous beam, so as to ablate a zone of a predetermined size on said target.

* * * * *